(12) United States Patent
Sevenster et al.

(10) Patent No.: US 11,495,343 B2
(45) Date of Patent: Nov. 8, 2022

(54) DEVICE, SYSTEM, AND METHOD FOR DETERMINING A READING ENVIRONMENT BY SYNTHESIZING DOWNSTREAM NEEDS

(71) Applicant: KONINKLIJKE PHILIPS N. V., Eindhoven (NL)

(72) Inventors: Merlijn Sevenster, Haarlem (NL); Paul Joseph Chang, Chicago, IL (US)

(73) Assignees: KONINKLIJKE PHILIPS N.V., Eindhoven (NL); UNIVERSITY OF CHICAGO, Chicago, IL (US)

(*) Notice: Subject to any disclaimer, the term of this patent is extended or adjusted under 35 U.S.C. 154(b) by 245 days.

(21) Appl. No.: 15/941,529

(22) Filed: Mar. 30, 2018

(65) Prior Publication Data

US 2018/0308575 A1 Oct. 25, 2018

Related U.S. Application Data

(60) Provisional application No. 62/488,358, filed on Apr. 21, 2017.

(51) Int. Cl.
*G16H 30/20* (2018.01)
*G16H 40/20* (2018.01)
*G16H 30/40* (2018.01)
*G16H 10/60* (2018.01)
*G06F 40/56* (2020.01)
*G16H 15/00* (2018.01)

(52) U.S. Cl.
CPC ............ *G16H 30/20* (2018.01); *G06F 40/56* (2020.01); *G16H 10/60* (2018.01); *G16H 15/00* (2018.01); *G16H 30/40* (2018.01); *G16H 40/20* (2018.01)

(58) Field of Classification Search
CPC ........ G16H 30/20; G16H 40/20; G16H 10/60; G16H 15/00; G16H 30/40; G06F 40/56
USPC .......................................................... 705/2
See application file for complete search history.

(56) References Cited

U.S. PATENT DOCUMENTS

| | | | |
|---|---|---|---|
| 6,272,495 B1 * | 8/2001 | Hetherington | G06F 16/3344 |
| 8,498,941 B2 * | 7/2013 | Felsher | G06F 21/6245 |
| | | | 705/51 |
| 11,244,755 B1 * | 2/2022 | Syeda-Mahmood | G06F 40/40 |

(Continued)

OTHER PUBLICATIONS

Ip, I.V. et al., "Adoption and Meaningful Use of Computerized Physician Order Entry with an Integrated Clinical Decision Support System for Radiology: Ten-Year Analysis in an Urban Teaching Hospital". Journal of the American College of Radiology, Elsevier, Amsterdam, NL. vol. 9, Nr: 2, pp. 129-136, 2012.

*Primary Examiner* — Michael Tomaszewski
*Assistant Examiner* — Rachael Sojin Stone

(57) ABSTRACT

A device, system, and method determines a reading environment by synthesizing downstream needs. The method at a workflow server includes receiving a request from a physician device utilized by a referring physician, the request directed to performing an imaging procedure. The method includes determining at least one normalized need from the request, the normalized need corresponding to the referring physician. The method includes generating information to be included in a reading environment based on the at least one normalized need, the information assisting an image interpreter in interpreting the imaging procedure.

12 Claims, 3 Drawing Sheets

(56) References Cited

U.S. PATENT DOCUMENTS

| | | | |
|---|---|---|---|
| 2002/0092005 A1* | 7/2002 | Scales | G06F 8/443 |
| | | | 717/162 |
| 2003/0212580 A1* | 11/2003 | Shen | G06Q 50/22 |
| | | | 705/2 |
| 2009/0132287 A1* | 5/2009 | Spivey | G06Q 10/1095 |
| | | | 705/3 |
| 2011/0119212 A1* | 5/2011 | De Bruin | G16H 50/70 |
| | | | 706/12 |
| 2015/0161329 A1 | 6/2015 | Mabotuwana | |
| 2015/0199946 A1* | 7/2015 | Kato | G09G 5/006 |
| | | | 348/14.12 |
| 2017/0091320 A1* | 3/2017 | Psota | G06F 16/35 |
| 2018/0308575 A1* | 10/2018 | Sevenster | G06F 40/56 |
| 2021/0158931 A1* | 5/2021 | Tweedie | G16H 10/20 |
| 2021/0216822 A1* | 7/2021 | Paik | G06F 3/013 |

* cited by examiner

DEVICE, SYSTEM, AND METHOD FOR DETERMINING A READING ENVIRONMENT BY SYNTHESIZING DOWNSTREAM NEEDS

BACKGROUND INFORMATION

A physician may provide healthcare services to patients using a variety of different procedures and recommending a variety of different treatments. The physician may tailor the healthcare services for the patient based on a diagnosis determined by the physician using any available information of the patient. For example, the physician may receive answers to medically related questions, personally examine particular body areas, refer to other test results of the patient, etc. When using a test result from a procedure performed on the patient such as by an image interpreter, the physician may first recommend that the procedure be performed. Thus, the physician may refer the patient to the image interpreter such that the test result may be obtained and provided to the physician.

The image interpreter may capture images of a desired area of the patient using a variety of different procedures and a variety of different approaches. However, the referring physician may require images using a specific procedure and a specific approach. For example, a referring physician relies on quantitative data points extracted from imaging studies (e.g., an oncologist generally expects two-dimensional measurements of representative tumors). Unless this information is provided to the image interpreter and the image interpreter acknowledges this information, an image reading environment used by the image interpreter is likely to not be responsive to the needs and expectations of the referring physician. Accordingly, the burden of configuring the reading environment is placed on the image interpreter to synthesize the downstream needs and expectations (of the referring physician) as well as to manually configure supportive technology to address these needs and expectations. This process is often laborious and time consuming for the image interpreter which increases the time required for results to be relayed back to the referring physician. In addition, as the number of available workflow solutions grows, the selection of the workflow and the manner to utilize the selected workflow for the reading environment becomes more challenging for the image interpreter.

An approach used to alleviate the efforts of the image interpreter in synthesizing the downstream needs and expectations of the referring physician is to enable the image interpreter to create and document quantitative data points more accurately and more efficiently. A conventional manner is a Measurement Assistant (MA) which is a picture archiving and communication system (PACS) workflow solution that allows an image interpreter to manage tumor measurements longitudinally. The MA persists the measurements electronically so that the measurements may be re-used in a format that is appropriate for the referring physician and allows generation of a free-text measurements section for inclusion in the narrative report.

Although the MA appears to provide a solution to the above described problem, the MA itself also has drawbacks that do not fully address the requirement of determining the downstream needs and expectations of the referring physician. For example, there must be an underlying assumption that the MA is universally adopted and used after installation, which is not guaranteed. In fact, studies have indicated that a conservative estimate for adoption of MA by radiologists reaches around 80% for tumor measurements read with MA. Even with encouragement features to utilize MA (e.g., educational sessions, gentle reminders, user-specific scorecards, etc.) and an auto-launch capability of MA, the use of MA does not reach universal adoption, particularly in view of the manual contribution needed for using MA. That is, there are still instances where the image interpreter is required to determine the downstream needs and expectations of the referring physician.

In a particular example, if a patient having an imaging procedure performed has no prior image examinations that were read with MA, the MA application does not auto-launch, even with such a capability enabled. The patient may not have prior image examinations for many reasons including being a new patient, a previous patient having new tumors, etc. Therefore, there is a problem with identifying the needs of the referring physician to the image interpreter. When the imaging procedure is eventually scheduled, there may be a lack of communication regarding the specifics of the imaging procedure that correlate to the needs of the referring physician.

SUMMARY

The present application is directed to a method, comprising: at a workflow server: receiving a request from a physician device utilized by a referring physician, the request directed to performing an imaging procedure; determining at least one normalized need from the request, the normalized need corresponding to the referring physician; and generating information to be included in a reading environment based on the at least one normalized need, the information assisting an image interpreter in interpreting the imaging procedure.

The present application is directed to a workflow server, comprising: a transceiver communicating via a communications network, the transceiver configured to exchange data with a physician device utilized by a referring physician and an image interpreter device utilized by an image interpreter; a memory storing an executable program; and a processor that executes the executable program that causes the processor to perform operations, comprising, receiving a request from a physician device utilized by a referring physician, the request directed to performing an imaging procedure; determining at least one normalized need from the request, the normalized need corresponding to the referring physician; and generating information to be included in a reading environment based on the at least one normalized need, the information assisting an image interpreter in interpreting the imaging procedure.

The present application is directed to a method, comprising: at a workflow server: receiving a request from a physician device utilized by a referring physician, the request directed to performing an imaging procedure; determining at least one normalized need from the request, the normalized need corresponding to the referring physician; determining at least one workflow solution based on the at least one normalized need, the at least one workflow solution respectively associated with defining a manner that the imaging procedure is to be performed; and generating a reading environment based on the at least one normalized need, the reading environment providing the at least one workflow solution.

DETAILED DESCRIPTION

Figure 1:
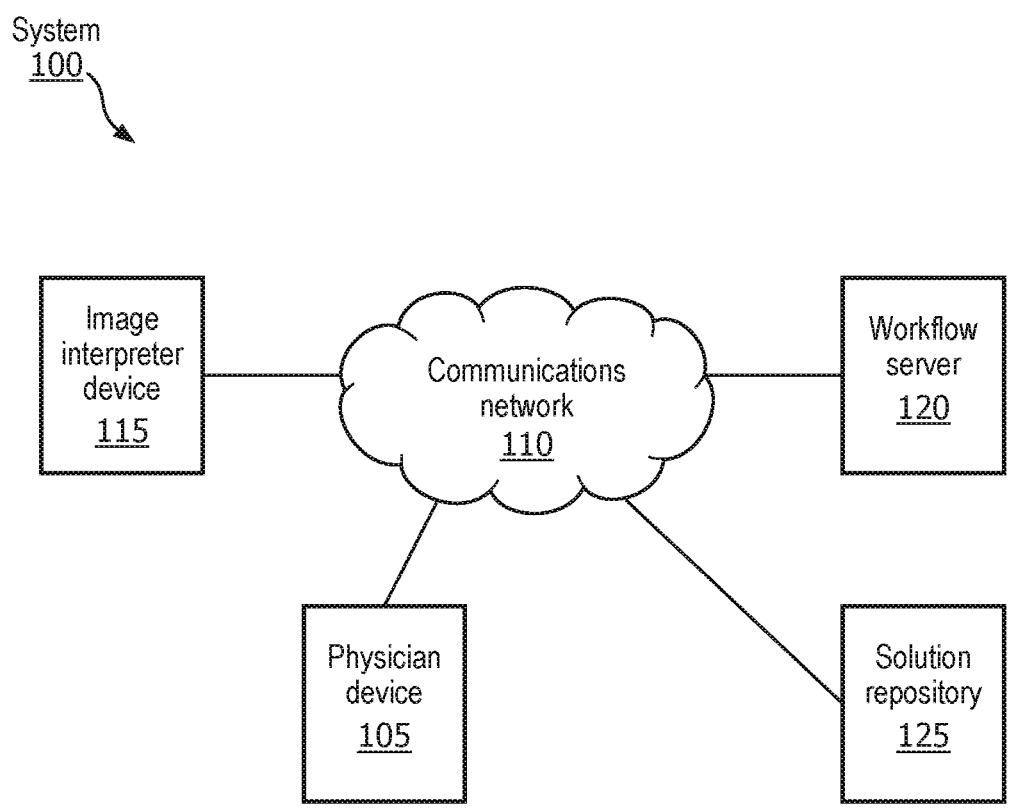
FIG. 1 shows a system according to the exemplary embodiments.

The exemplary embodiments may be further understood with reference to the following description and the related appended drawings, wherein like elements are provided with the same reference numerals. The exemplary embodiments are related to a device, a system, and a method for imaging procedures to be more efficiently performed on a patient by an image interpreter based on needs and/or expectations of a referring physician. Specifically, the exemplary embodiments are configured to automatically detect the needs/expectations of a referring physician and automatically configure or modify a reading environment based on these needs/expectations for the image interpreter. Accordingly, the image interpreter is not required to determine any downstream needs of the referring physician. In this manner, the image interpreter may perform the imaging procedure with the provided reading environment and return the test results to the referring physician which satisfy the physician's requirements.

It is noted that the exemplary embodiments are described with regard to a reading environment for an image interpreter with downstream needs relating to a referring physician. However, the image interpreter, the imaging procedure, and the reading environment are only exemplary. The exemplary embodiments may be modified to be used with any process flow in which a referring physician has a set of needs/expectations and this information is used as a basis for a further clinician to perform a procedure and generate results. It is also noted that the connection to the medical field is only exemplary. The exemplary embodiments may also be modified to be used with any process flow in which a first user has a set of needs/expectations and a second user performs an operation and generates results based on this information.

As used herein, the referring physician has needs and/or expectations with regard to results provided by the image interpreter. These needs and expectations may represent or cover any need, expectation or other value extracted from an imaging interpretation, created by image interpreter interaction with the image examination, and documented in the imaging report and/or any workflow solution. These needs/expectations are hereinafter collectively referred to as "needs."

For illustrative purposes, the exemplary embodiments may assume a presence of and access to one or more workflow solutions. For example, the workflow solutions may include longitudinal quantification technology, image segmentation technology, computer-aided detection technology, computer-aided diagnosis technology, guideline-based recommendation technology, search technology, etc. Accordingly, the workflow solution may be any automated application that assists an image interpreter in interpreting images captured using an imaging procedure. However, the selection and use of existing workflow solutions is only exemplary and the exemplary embodiments may be modified to determine and/or create a workflow solution to be used in the reading environment. The exemplary embodiments also utilize reading environments that are used with various imaging procedures. However, the exemplary embodiments may be modified to determine and create the reading environment as well.

FIG. 1 shows a system 100 according to the exemplary embodiments. The system 100 relates to a communication between various components involved in providing healthcare to a patient. Specifically, the system 100 may relate to a scenario when a physician refers the patient to an image interpreter for an imaging procedure to be performed to generate test results that are returned to the referring physician. The system 100 may include a physician device 105, a communications network 110, and an image interpreter device 115. As will be described in further detail below, the system 100 is configured to modify a reading environment to include information that assists the image interpreter in interpreting an imaging procedure where the information may include workflow solutions that correspond to the needs of the referring physician. Accordingly, the system 100 may also include a workflow server 120 and a solution repository 125.

The physician device 105 may represent any electronic device that is configured to perform the functionalities associated with a physician. For example, the physician device 105 may be a portable device such as a tablet, a laptop, etc. or a stationary device such as a desktop terminal. The physician device 105 may include the necessary hardware, software, and/or firmware to perform the various operations associated with medical treatment. The physician device 105 may also include the required connectivity hardware, software, and firmware (e.g., transceiver) to establish a connection with the communications network 110 to further establish a connection with the other components of the system 100.

The physician device 105 may be configured to enable the physician to perform the various operations associated with medical treatment. For example, the physician device 105 may schedule appointments for patients using a calendar application, may track treatments or procedures of a patient, etc. In another example, the physician device 105 may schedule or request an imaging procedure to be performed on the patient. That is, the physician device 105 may recommend the imaging procedure to the patient and, when the patient agrees, it may refer the patient to an image interpreter to perform the imaging procedure. Thus, the physician may utilize the physician device 105 to enter the request along with any other information. In a further example and as will become apparent below, the physician device 105 may receive test results associated with an imaging procedure and display the results to the physician.

The communications network 110 may be configured to communicatively connect the various components of the system 100 to exchange data. The communications network 110 may represent any single or plurality of networks used by the components of the system 100 to communicate with one another. For example, if the physician device 105 is used at a hospital, the communications network 110 may include a private network with which the physician device 105 may initially connect (e.g. a hospital network). The private network may connect to a network of an Internet Service Provider to connect to the Internet. Subsequently, through the Internet, a connection may be established to other electronic devices. For example, the workflow server 120 may be remote relative to the hospital but may be connected to the Internet. Thus, the physician device 105 may be communicatively connected to the workflow server 120. It should be noted that the communications network 110 and all networks that may be included therein may be any type of network. For example, the communications network 110 may be a local area network (LAN), a wide area network (WAN), a virtual LAN (VLAN), a WiFi network, a HotSpot, a cellular network (e.g., 3G, 4G, Long Term Evolution (LTE), etc.), a cloud network, a wired form of these networks, a wireless form of these networks, a combined wired/wireless form of these networks, etc.

The image interpreter device 115 may represent any electronic device that is configured to perform the functionalities associated with an image interpreter. For example, like the physician device 105, the image interpreter device 115 may be a portable device such as a tablet, a laptop, etc., or a stationary device such as a desktop terminal. The image interpreter device 115 may also include the necessary hardware, software, and/or firmware to perform the various operations associated with imaging procedures. The image interpreter device 115 may also include the required connectivity hardware, software, and firmware (e.g., transceiver) to establish a connection with the communications network 110 to further establish a connection with the other components of the system 100.

The image interpreter device 115 may be configured to enable the image interpreter to perform the various operations associated with imaging procedures. As those skilled in the art will understand, there are a plurality of different imaging procedures that may be performed using different imaging modalities. For example, the imaging procedures may be an X-ray procedure, a computed tomography (CT) procedure, a magnetic resonance imaging (MRI) procedure, an ultrasound procedure, a positron emission tomography (PET) scan procedure, a single-photon emission computed tomography (SPECT) scan procedure, or hybrids thereof, and etc. Each imaging procedure may utilize a reading environment upon which the image interpreter may capture and interpret images. As will be described in further detail below, the image interpreter device 115 may receive information that is included in the reading environment from the workflow server 120 that assists the image interpreter in interpreting the imaging procedure (e.g., the manner in which the imaging procedure is to be performed for the patient). The image interpreter device 115 may continuously exchange data with the workflow server 120 during the time the imaging procedure is being performed such as inputs provided by the image interpreter. Once the imaging procedure is completed, the image interpreter device 115 may transmit the test results of the imaging procedure to the physician device 105.

The workflow server 120 may be a component of the system 100 that performs functionalities associated with determining the information that is to be included in the reading environment according to the exemplary embodiments. As will be described in further detail below, the workflow server 120 may receive a request or information from a referring physician utilizing the physician device 105, determine information (e.g., workflow solutions) to be included in the reading environment based on the needs of the referring physician, and provide the modified reading environment to the image interpreter device 115 for an imaging procedure to be performed. The workflow server 120 may utilize various functionalities and operations as well as workflow solutions to determine the reading environment. The functionalities and operations of the workflow server 120 in determining information that is included in the reading environment may be performed as a preliminary step and/or during a time the image interpreter is performing the imaging procedure.

The solution repository 125 may represent any source from which workflow solutions are stored and retrieved by the workflow server 120. As described above, the workflow solutions may be based on longitudinal quantification technology, image segmentation technology, computer-aided detection technology, computer-aided diagnosis technology, guideline-based recommendation technology, search technology, etc. Accordingly, the solution repository 125 may be sources upon which these various technologies perform their respective functionalities to provide a corresponding output of a workflow solution. In another exemplary embodiment, the solution repository may be a data storage component that stores the workflow solutions from further electronic components that utilize these various technologies. The solution repository 125 may store existing workflow solutions that may be selected for use with the information included in the reading environment according to the exemplary embodiments. However, it is again noted that the workflow server 120 may be modified to determine and create a workflow solution that is to be used in the reading environment.

It should be noted that the system 100 illustrating a single solution repository 125 is only exemplary. The solution repository 125 may represent one or more sources of workflow solutions that may be accessed by the workflow server 120. For example, the technologies upon which the workflow solutions are generated may each have a respective solution repository 125. In another example, a plurality of technologies may be provided by a single source such that a single solution repository 125 may be used for these plurality of technologies.

It is also noted that the system 100 may also include a plurality of physician devices 105, a plurality of image interpreter devices 115, and a plurality of workflow servers 120. That is, many different physicians and image interpreters may utilize the system 100. There may also be many different workflow servers 120 that service different physician devices 105 and image interpreter devices 115.

Figure 2:
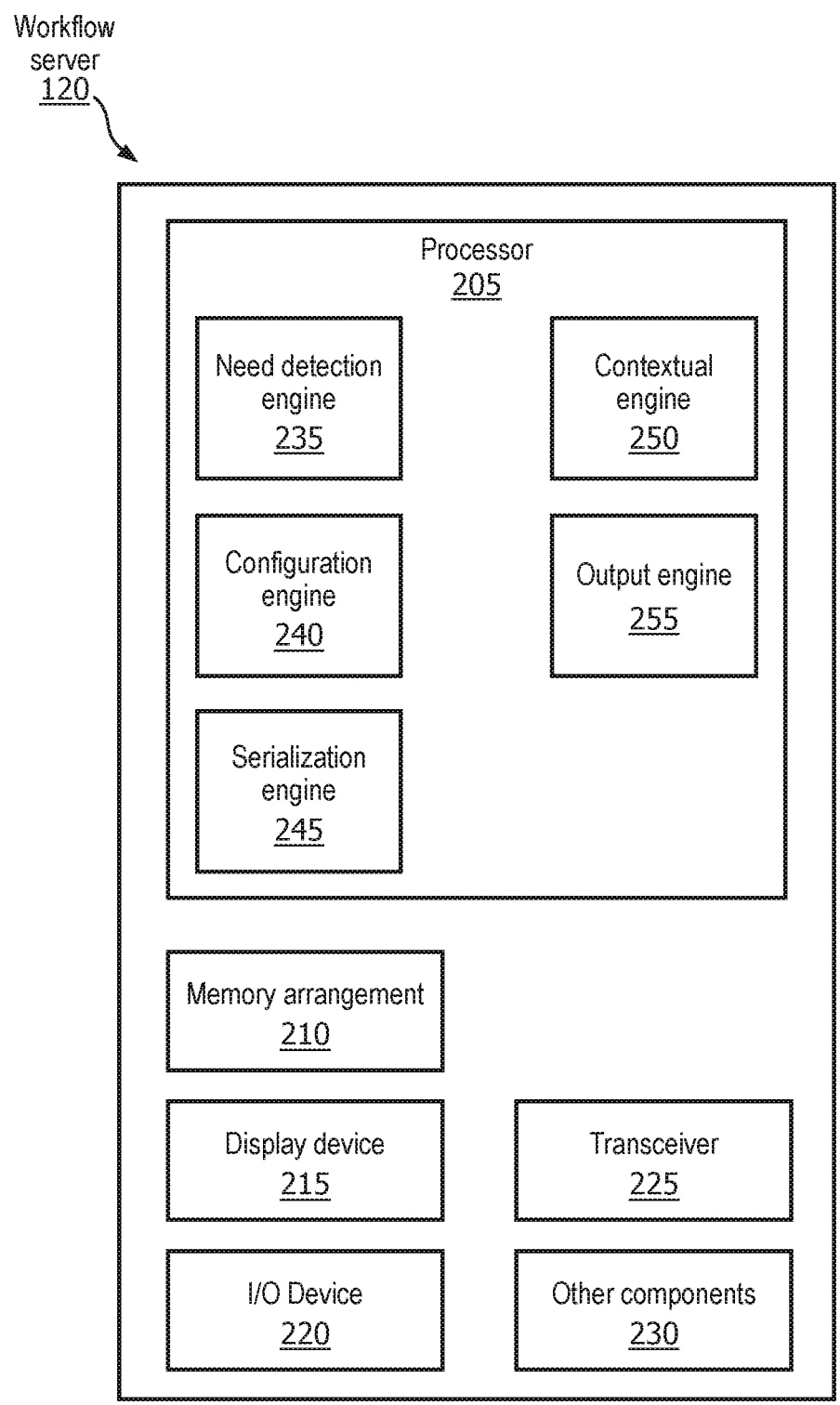
FIG. 2 shows a workflow server of FIG. 1 according to the exemplary embodiments.

As described above, the workflow server 120 may determine the reading environment based on the needs of the referring physician. FIG. 2 shows the workflow server 120 of FIG. 1 according to the exemplary embodiments. The workflow server 120 may provide various functionalities in determining the information to be included in the reading environment. Although the workflow server 120 is described as a network component (specifically a server), the workflow server 120 may be embodied in a variety of hardware components such as a portable device (e.g., a tablet, a smartphone, a laptop, etc.) or a stationary device (e.g., a desktop terminal). The workflow server 120 may be incorporated into the physician device 105 and/or the image interpreter device 115, or incorporated into a website service, etc. The workflow server 120 may include a processor 205, a memory arrangement 210, a display device 215, an input and output (I/O) device 220, a transceiver 225, and other components 230 (e.g., an imager, an audio I/O device, a battery, a data acquisition device, ports to electrically connect the workflow server 120 to other electronic devices, etc.).

The processor 205 may be configured to execute a plurality of applications of the workflow server 120. As will be described in further detail below, the processor 205 may utilize a plurality of engines including a need detection engine 235, a configuration engine 240, a serialization engine 245, a contextual engine 250, and an output engine 255. The need detection engine 235 may be configured to capture and normalize the needs of the referring physician. The configuration engine 240 may be configured to map the normalized needs of the referring physician onto an array of workflow solutions. The serialization engine 245 may be configured to serialize workflow solutions to ensure presentation of the workflow solutions in an appropriate order. The contextual engine 250 may be configured to prioritize the use of workflow technology based on contextual cues. The output engine 255 may be configured to generate the information to be included in a reading environment based on information from the other engines 235-250.

It should be noted that the above noted applications and engines each being an application (e.g., a program) executed by the processor 205 is only exemplary. The functionality associated with the applications may also be represented as components of one or more multifunctional programs, a separate incorporated component of the workflow server 120 or may be a modular component coupled to the workflow server 120, e.g., an integrated circuit with or without firmware.

The memory 210 may be a hardware component configured to store data related to operations performed by the workflow server 120. Specifically, the memory 210 may store data related to the various engines 235-255 such as the request and the needs of the referring physician. The display device 215 may be a hardware component configured to show data to a user while the I/O device 220 may be a hardware component that enables the user to enter inputs. For example, an administrator of the workflow server 120 may maintain and update the functionalities of the workflow server 120 through user interfaces shown on the display device 215 with inputs entered with the I/O device 220. It should be noted that the display device 215 and the I/O device 220 may be separate components or integrated together such as a touchscreen. The transceiver 225 may be a hardware component configured to transmit and/or receive data via the communications network 110.

According to the exemplary embodiments, the workflow server 120 may perform various different operations to determine the information to be included in the reading environment that is used by the image interpreter to generate test results for the referring physician. Initially, as described above, the need detection engine 235 may be configured to capture and normalize the needs of the referring physician. Accordingly, the referring physician may utilize the physician device 105 to enter a request for an imaging procedure. The request may be transmitted to the workflow server 120. Specifically, the need detection engine 235 may receive the request that is provided in the context of ordering the imaging procedure. The need detection engine 235 may subsequently convert the request into a series of normalized needs corresponding to the referring physician. For example, a first physician may have a first set of needs to view an area of the patient whereas a second physician may have a second set of needs to view the same area of the patient. If the first physician were to enter the request, the first set of needs would be used as the basis of determining the reading environment.

In a specific implementation of the need detection engine 235 according to the exemplary embodiments, a predetermined data scheme may be used. The predetermined data scheme may list all potential needs of referring physicians. More particularly, the needs of the predetermined data scheme may be hierarchically structured. For example, the needs of the predetermined data scheme may include a tree structure in which the referring physician requires an image quantification from an imaging procedure. Accordingly, a first level of needs may be labeled as "image quantification." The image quantification may include sub-requirements such as oncological and vascular. Accordingly, a second level of needs under "image quantification" may be "oncological" and "vascular." The oncological sub-requirement may also include sub-requirements such as standards set forth by the World Health Organization (WHO), the Response Evaluation Criteria in Solid Tumors (RECIST) 1.0, and RECIST 1.1. Accordingly, a third level of needs under "oncological" may be "WHO," "RECIST 1.0," and "RECIST 1.1."

The need detection engine 235 may receive the request from the physician device 105 in a variety of manners. In a first example, the referring physician may enter text that provides information relating to the imaging procedure being requested. For example, the referring physician may enter text on the physician device 105 to describe a patient history, current symptoms, the reason for the imaging procedure, clinical questions, etc. The referring physician may also elaborate on the reason for the imaging procedure to capture downstream needs (e.g., "Please make RECIST measurements."). When this text is entered by the referring physician on the physician device 105, the physician device 105 may subsequently transmit this data to the workflow server 120.

When the workflow server 120 receives the request from the physician device in this format, the need detection engine 235 may filter the data using natural language processing operations that normalize the terms for mapping onto the needs of the predetermined data scheme. The needs of the predetermined data scheme may be organized as a list of keywords and/or key phrases. Accordingly, the lexical elements of the terms from the request may be used to perform a search on the normalized needs of the predetermined data scheme such as with pre-processing techniques (e.g., stemming). In a particular example, if the reason for the imaging procedure contains the term "RECIST" which has been identified by the need detection engine 235, the need detection engine 235 may map this term to a normalized need corresponding to "Response Evaluation Criteria in Solid Tumors 1.1." The need detection engine 235 may support further operation in filtering the data of the request and mapping to the normalized needs. For example, the need detection engine 235 may utilize a negation detection operation, a concept extraction operation, etc.

In a second example of receiving the request, the workflow server 120 may provide a dedicated user interface environment to the physician device 105. The dedicated user interface environment may enable the referring physician to mark any needs in an electronic and structured manner. For example, the needs of the predetermined data scheme may be presented on the physician device 105 to the referring physician as a tree structure wherein items are selectable. The dedicated user interface environment may integrate dynamic and predetermined operations in receiving inputs from the referring physician. In an exemplary operation, the need detection engine 235 may take into account a specialty of the referring physician and filtering the normalized needs of the predetermined data scheme using a mapping for this specialty. For example, if the referring physician is an oncologist, the referring physician may select a first need as "Quantification" which may lead to a following need of "Oncological" whereas another referring physician whose specialty is cardiology will not be presented "Oncological" (but may instead be presented with "Cardiological").

In a third example, the need detection engine 235 may utilize profiles. In a first example of using profiles, the need detection engine 235 may store a plurality of dedicated profiles where each dedicated profile includes a combination of normalized needs of the predetermined data scheme. Each dedicated profile may be assigned a header that may be retrieved by selecting the profile specifically from a dedicated user interface. For example, the header may state "Research protocol XYZ," "Standard Oncological Quantification," etc. In a second example of using profiles, the need detection engine 235 may store a user profile for the referring physician that includes a combination of normalized needs of the predetermined data scheme. Thus, if a referring physician has a request for an imaging procedure and a common set of needs are used by the referring physician, the referring physician may select the user profile (which may include or exclude normalized needs that are part of dedicated profiles). However, if the referring physician should require a different set of needs, the referring physician may override a selection of the user profile. The user profile may be created manually or automatically. For example, the referring physician may manually select the normalized needs to be included in the user profile. In another example, based on previously selected normalized needs or dedicated profiles, the need detection engine 235 may create the user profile to include a personalized set of normalized needs.

The configuration engine 240 maps the normalized needs of the referring physician onto an array of workflow solutions. As described above, the workflow server 120 may have access to the solution repository 125 which stores a plurality of workflow solutions that are based on a variety of different technologies. Again, the workflow solutions may be any automated application that assists the image interpreter in interpreting captured images from the imaging procedure. For example, the workflow solution may define settings in which the images are to be captured, a position/angle in which the images are to be captured, etc. The configuration engine 240 may be configured to receive the normalized needs from the need detection engine 235 and determine whether the normalized needs may be mapped onto one or more workflow solutions. Accordingly, depending on the normalized needs, the configuration engine 240 may map to zero workflow solutions, one workflow solution, or more than one workflow solutions.

According to an exemplary embodiment, the configuration engine 240 may leverage a mapping table that associates the normalized needs received from the need detection engine 240 with workflow solutions addressing the needs. For example, the configuration engine 240 may map the need for RECIST 1.1 measurements onto a picture archiving and communication system (PACS) workflow solution. Once mapped, the output of the configuration engine 240 may be an array of Booleans that indicate whether the workflow solution associated with a particular cell in the array is to be activated. In this manner, each workflow solution that is included for consideration may be activated or remain deactivated through the mapping performed by the configuration engine 240.

In a further feature, the configuration engine 240 may utilize more specific information that is stored to configure the reading environment of the image interpreter as well as the individual workflow solutions. For example, the PACS workflow solution may be configured differently depending on whether the normalized need is WHO, RECIST 1.0, or RECIST 1.1. Specifically, the WHO guideline utilizes uni-dimensional measurements whereas the RECIST 1.1 utilizes bi-dimensional measurements. Thus, if the need is identified and normalized to correspond to RECIST 1.1, the configuration engine 240 may provide a signal to a subsequent component (e.g., the output engine 255) to indicate that the image interpreter may be alerted that a finding which was measured in only one dimension requires that another measurement be made.

The serialization engine 245 serializes workflow solutions to ensure presentation of the workflow solutions in an appropriate order. Initially, the serialization engine 245 may provide an enhanced feature that is utilized for the information that is included in the reading environment according to the exemplary embodiments. That is, the workflow server 120 may be configured to omit the use of the serialization engine 245 such as when zero or only one workflow solution has been mapped to the normalized needs. In another example, the workflow server 120 may be configured to omit the use of the serialization engine 245 when a serial dependency (as described below) does not exist.

The workflow solutions that may be utilized by the workflow server 120 may have a serial dependency. That is, a first workflow solution may be required prior to a second workflow solution being available for use. For example, the first workflow solution may be associated with imaging a general area and the second workflow solution may be associated with a more specific imaging within the general area. Thus, without first imaging the general area, the second workflow solution cannot be logically used. In this manner, the output of the first workflow solution may be required as an input for the second workflow solution. It is noted that this serial dependency may only apply to certain workflow solutions since one or more workflow solutions may stand independently with no relationship to other workflow solutions.

When a serial dependency does exist between the workflow solutions mapped by the configuration engine 240, the serialization engine 245 may generate a signal for a subsequent component (e.g., the output engine 255) to present the first workflow solution prior to the second workflow solution. That is, the second workflow solution should not be launched prior to the first workflow solution. The serialization engine 245 may utilize a table of all relationships between the available workflow solutions such that identification of any workflow solution having a serial dependency may result in an ordering to be identified or whether another workflow solution may be required to be added (e.g., when the output of the first workflow solution is required for the second workflow solution but only the second workflow solution was mapped). The serialization engine 245 may then structure the workflow solutions found by the configuration engine 240 by retrieving their pairwise dependencies. The result may be represented as a non-cyclic graph.

The contextual engine 250 prioritizes the use of workflow technology based on contextual cues. Initially, substantially similar to the serialization engine 245, the contextual engine 250 may provide an enhanced feature that is utilized in further developing the reading environment according to the exemplary embodiments. That is, the workflow server 120 may be configured to omit the use of the functionalities of the contextual engine 250. For example, as will be described in detail below, the contextual engine 250 operates with the output engine 255 since inputs received from the image interpreter are utilized by the contextual engine 250. Thus, if the image interpreter device 115 utilizes a reading environment provided by the output engine 255 without exchanging data with the workflow server 120 and only provides the test results after the imaging procedure is completed, the features of the contextual engine 250 may not be utilized.

The contextual engine 250 may prioritize the relevant workflow solutions based on contextual cues. The contextual cues may be any input from the image interpreter device 115 entered by the image interpreter performing the imaging procedure. The context cues may include any type of input such as cursor movements (e.g., via a mouse), text inputs (e.g., via a keyboard), selections of images/areas, etc. The contextual engine 250 may mediate between the intent of the image interpreter and the workflow support technology of the workflow solutions. Accordingly, the contextual engine 250 may be leveraged by feeding the output of the configuration engine 240 to prioritize the relevant workflow solutions based on contextual cues that are gathered. For example, if the intent of the image interpreter is identified and/or the normalized needs of the referring physician are provided as (1) creating a measurement where the measured object is oncological (e.g., through lesion characterization) and (2) including an oncological quantification, the contextual engine 250 may launch the associated workflow solution.

The output engine 255 generates the information to be included in the reading environment based on information from the other engines 235-250. Specifically, the information may be the workflow solutions determined by the other engines 235-250, a representation of the workflow solutions, keywords of the needs of the referring physician, etc. The output engine 255 may transmit an output to the image interpreter device 115 prior to the image procedure being performed. Thus, when the image interpreter begins the imaging procedure, the image interpreter device 115 may launch the output that shows the reading environment upon which the imaging procedure is to be performed. For example, when one or more workflow solutions were mapped by the configuration engine 240, the output may include these relevant workflow solutions which are shown to the image interpreter for the imaging procedure to proceed accordingly. In another example, when no workflow solution is mapped, the output may include normalized needs which are shown to the image interpreter such that the imaging procedure may be performed with these normalized needs as a consideration.

The reading environment may include a dedicated area in which the relevant workflow solutions are docked (e.g., positioned in the reading environment). That is, the exemplary embodiments may select a location for the dedicated area and provide the information in the dedicated area of the reading environment. Another area of the reading environment may be to show the images captured by the imaging procedure. If there are no workflow solutions considered relevant, the area may be collapsed. If the serialization engine 245 is being utilized, the workflow solutions that do not require an input from another workflow solution may be docked until such input becomes available (in which the following workflow solution may be docked). The docking area may be updated dynamically. For example, if one workflow solution has been used that provides input to another, the following workflow solution may be launched after the prior workflow solution is closed. When the contextual engine 250 is being utilized, a prioritization of workflow solutions may be provided. For example, based on how the contextual engine 250 cooperates with the output engine 255, only one, at most two, at most three, at most four, etc. workflow solutions may be shown at the same time. In another example, only workflow solutions whose estimated relevance exceeds a predetermined threshold may be shown. In a further example, based on the contextual cues being received from the image interpreter device 115, workflow solutions that are associated with the contextual cues may be updated dynamically in view of these contextual cues.

Using the above mechanism of the workflow server 120, the exemplary embodiments provide the proper identification of how an imaging procedure is to be performed by an image interpreter to generate the appropriate test results for the referring physician. When the referring physician places a request for the imaging procedure, the need detection engine 235 may determine the normalized needs of the request for the referring physician. The configuration engine 240 may then map the normalized needs to workflow solutions that are to be used in the reading environment by the image interpreter. The serialization engine 245 may be utilized to order the workflow solutions, if applicable. The output engine 255 receives the outputs from these engines and generates the information to be included in the reading environment to be viewed by the image interpreter. The contextual engine 250 may be utilized to dynamically update the workflow solutions of the reading environment, if applicable. In this manner, the image interpreter may perform or interpret the imaging procedure using the workflow solutions that are shown in the reading environment. Since the workflow solutions are selected based on the needs of the referring physician, the test results of the imaging procedure that are generated and returned to the referring physician are expected to meet any requirements of the referring physician.

It is noted that the test results of the imaging procedure may be provided to the referring physician in a variety of ways. For example, the test results may be mailed (e.g., electronically) to the referring physician. In another example, the image interpreter device 115 may be configured to transmit the test results to a network storage component or network service. Thereafter, the referring physician (or any other authorized user) may access and/or retrieve the test results. In a further example, the workflow serer 120 may include a further component (e.g., a transfer engine) that performs the functionality of forwarding the test results from the image interpreter device 115 to the physician device 105.

Figure 3:
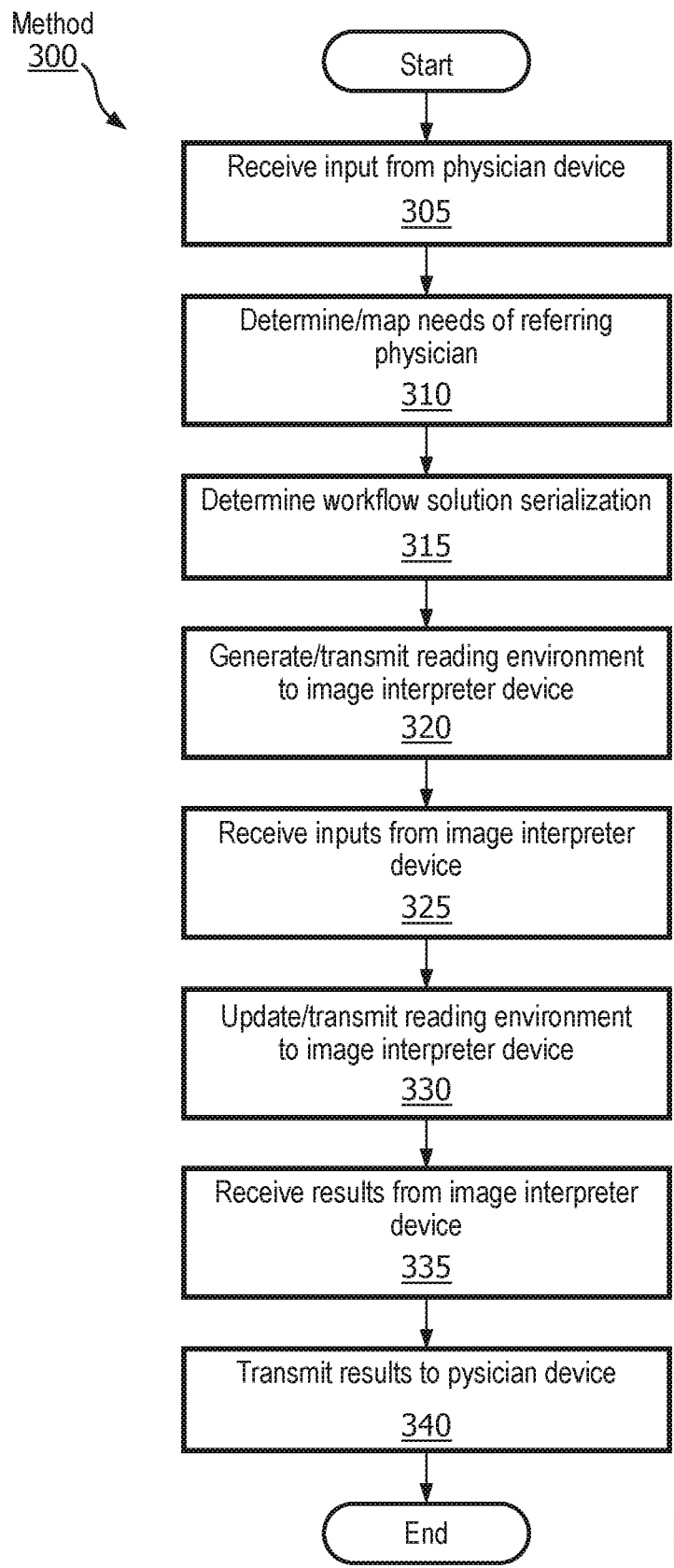
FIG. 3 shows a method for determining a reading environment according to the exemplary embodiments.

FIG. 3 shows a method 300 for determining a reading environment according to the exemplary embodiments.

Specifically, the method 300 may relate to the mechanism of the exemplary embodiments in which the reading environment used by an image interpreter in performing an imaging procedure is prepared based on needs of a referring physician. Accordingly, the method 300 will be described from the perspective of the workflow server 120. The method 300 will also be described with regard to the system 100 of FIG. 1 and the plurality of engines 235-255 of the workflow server 120 of FIG. 2.

For illustrative purposes, it may be assumed that the physician device 105, the image interpreter device 115, the workflow server 120, and the solution repository 125 are all communicatively connected to one another (e.g., via the communications network 110). It may also be assumed that the physician device 105 and the image interpreter device 115 each have an application launched thereon that operates in cooperation with the workflow server 120.

In step 305, the workflow server 120 receives an input from the physician device 105. Specifically, the workflow server 120 may receive a request from the physician device 105. As described above, the referring physician may enter a request and/or other information onto the physician device 105. The request and the other information may be forwarded to the workflow server 120 prior to the request being serviced. The request may be provided by the referring physician using a variety of different mechanisms. In a first example, the request may be entered with free text. In a second example, the request may be entered using a dedicated user interface environment.

In step 310, the workflow server 120 determines the needs of the referring physician. As described above, the needs of the referring physician may be determined based on the request and/or the other information provided from the physician device 105. Based on the manner in which the request and the other information is received, the workflow server 120 may identify normalized needs from a predetermined data scheme. For example, when the request is entered with free text, the workflow server 120 may utilize natural language processing to determine keywords or phrases to identify the normalized needs. In another example, when the request is entered with the dedicated user interface environment, a direct correlation between the selections on the dedicated user interface environment and the normalized needs may be determined. In a further example, the other information such as identifying information of the physician device 105 or the referring physician may be used to identify a user profile. In yet another example, the request and/or the identity of the referring physician may be used to identify a dedicated profile having a predetermined set of normalized needs.

Also in step 310, the workflow server 120 may map the normalized needs of the referring physician. Specifically, the workflow server 120 may map the normalized needs to any relevant workflow solutions. As described above, the workflow solutions may be stored in the solution repository. In a particular example, the workflow solutions may each have an associated set of keywords or phrases that identify a relevance. When at least a minimum number of these associated keywords/phrases are included in the normalized needs, the workflow server 120 may determine whether the workflow solution is to be selected for mapping. The workflow server 120 may also track a relevance value which is determined based on a correlation of the associated keywords/phrases to the normalized needs. Thus, when the relevance value is above a predetermined threshold, the workflow server 120 may map the workflow solution and include the workflow solution as part of the reading environment. It is again noted that it may be possible that only one or no workflow solution is identified.

In step 315, the workflow server 120 determines a workflow solution serialization. As described above, when more than one workflow solution is identified, the workflow server 120 may utilize a feature in which a serialization or ordering of the workflow solutions may be identified. Initially, it is again noted that even when more than one workflow solution is identified, there may be no serialization. For example, all workflow solutions may be independent and not rely on any output of another workflow solution. However, if a serial dependency is identified between two or more workflow solutions, the workflow server 120 may track this serialization that is applied to the reading environment.

The method 300 may be modified to address when no serial dependency exists or when only one or no workflow solutions are identified. For example, prior to step 315, the method 300 may include a step that determines whether there is less than two workflow solutions identified. If less than two workflow solutions are identified, the method 300 may omit step 315 and continue to step 320. However, when more than one workflow solution is identified, the method 300 may consider step 315. In another example, when more than one workflow solution is identified, the method 300 may include a step that determines whether there is any serial dependency among the workflow solutions. In a particular embodiment, each workflow solution may have any serial dependency that is predetermined and associated therewith. Thus, identification of any workflow solution having an associated dependency may identify a serial dependency.

In step 320, the workflow server 120 generates the information to be included in the reading environment and transmits the modification for the reading environment to the image interpreter device 115. The image interpreter device 115 may be configured to incorporate the information into the reading environment that is being viewed by the image interpreter. Alternatively, the workflow server 120 may generate and transmit a modified reading environment (including the information) to the image interpreter device 115. Based on the workflow solutions that are identified from the normalized needs of the referring physician, the reading environment in which the image interpreter is to use to perform the imaging procedure may be provided. For example, a predetermined area of the reading environment may show any workflow solution.

In step 325, the workflow server 120 receives inputs from the image interpreter device 115. As described above, the workflow server 120 may include another enhanced feature in which contextual cues from the image interpreter are used to dynamically update or modify the reading environment and/or the workflow solutions. Thus, during the course of performing the imaging procedure as well as utilizing the reading environment as provided previously, any contextual cues may be received. When received, in step 330, the workflow server 120 updates/transmits the reading environment to the image interpreter device 115.

When the imaging procedure has completed, in step 335, the workflow server 120 receives the test results from the image interpreter device 115. As described above, one implementation of the exemplary embodiments relates to the workflow server 120 including a functionality of forwarding the test results from the image interpreter device 115 to the physician device 105. Accordingly, when the workflow server 120 receives the test results, in step 340, the workflow server 120 transmits the test results to the physician device 105. Since the imaging procedure was performed with consideration of the needs of the referring physician, the test results also incorporate the needs of the referring physician.

The exemplary embodiments provide a device, system, and method of generating test results of an imaging procedure that match the needs of a referring physician. Specifically, when a request for an imaging procedure is made for a patient by the referring physician, a workflow server determines the needs of the referring physician. Based on these needs, the workflow server may identify workflow solutions or manner in which an image interpreter is to perform the imaging procedure. Accordingly, using a needs based defined imaging procedure, test results therefrom meet any requirements of the referring physician.

Those skilled in the art will understand that the above-described exemplary embodiments may be implemented in any suitable software or hardware configuration or combination thereof. An exemplary hardware platform for implementing the exemplary embodiments may include, for example, an Intel x86 based platform with compatible operating system, a Windows platform, a Mac platform and MAC OS, a mobile device having an operating system such as iOS, Android, etc. In a further example, the exemplary embodiments of the above described method may be embodied as a computer program product containing lines of code stored on a computer readable storage medium that may be executed on a processor or microprocessor. Computer readable storage medium is included in hardware. Computer program product containing lines of code includes for example software or firmware. The storage medium may be, for example, a local or remote data repository compatible or formatted for use with the above noted operating systems using any storage operation.

It will be apparent to those skilled in the art that various modifications may be made in the present disclosure, without departing from the spirit or the scope of the disclosure. Thus, it is intended that the present disclosure cover modifications and variations of this disclosure provided they come within the scope of the appended claims and their equivalent.

What is claimed is:

1. A method, comprising:
   at a workflow server:
   receiving a request from a physician device utilized by a referring physician, the request directed to performing an imaging procedure;
   determining at least one normalized need from the request filtered from a set of normalized needs associated with a predetermined data scheme listing the needs of the referring physician in a hierarchical structure based on the specialty of the referring physician, the normalized need corresponding to the referring physician;
   generating a reading environment including a first area, a second area separate from the first area and information based on the at least one normalized need, the information assisting an image interpreter in interpreting the imaging procedure, wherein the first area in the reading environment is dedicated to the information and the second area in the reading environment is dedicated to showing images captured during the imaging procedure, wherein the information and the images do not overlap;
   mapping the at least one normalized need to workflow solutions, each workflow solution associated with a set of relevant keywords, wherein the mapping occurs when the set of relevant keywords of the at least one workflow solution is included in the one normalized need and a relevance value for the set of keywords is above a predetermined threshold;
   generating an updated reading environment based on the at least one workflow solution wherein the at least one workflow solution is included in the first area of the reading environment;
   generating a modified reading environment that incorporates the information into the reading environment
   transmitting the modified reading environment to an image interpreter device utilized by the image interpreter;
   receiving at least one contextual cue from the image interpreter device, wherein the at least one contextual cue comprises a specific mouse cursor gesture corresponding to a specific workflow solution; and
   updating the reading environment based on the at least one contextual cue.

2. The method of claim 1, further comprising:
   when the request is received in a free text format, performing a natural language processing operation to determine at least one keyword; and
   determining the at least one normalized need from the at least one keyword.

3. The method of claim 1, further comprising:
   when the request is received with at least one selection in a dedicated user interface, determining the at least one normalized need from the at least one selection.

4. The method of claim 1, further comprising:
   when the request is received with an identification, determining a profile, the profile including the at least one normalized need,
   wherein the profile is a dedicated profile, the identification being a dedicated header that identifies the dedicated profile, and
   wherein the profile is a user profile, the identification being an identity of the referring physician.

5. The method of claim 1, further comprising:
   when the at least one workflow solutions has a serial dependency, determining the serial dependency; and
   updating the reading environment based on the serial dependency.

6. The method of claim 1, further comprising:
   receiving test results from the imaging procedure; and
   transmitting the test results to the physician device.

7. A workflow server, comprising:
   a transceiver communicating via a communications network, the transceiver configured to exchange data with a physician device utilized by a referring physician and an image interpreter device utilized by an image interpreter;
   a memory storing an executable program; and
   a processor that executes the executable program that causes the processor to perform operations, comprising:
   receiving a request from a physician device utilized by a referring physician, the request directed to performing an imaging procedure;
   determining at least one normalized need from the request filtered from a set of normalized needs associated with a predetermined data scheme listing the needs of the referring physician in a hierarchical structure based on the specialty of the referring physician, the normalized need corresponding to the referring physician;
   generating a reading environment including a first area, a second area separate from the first area and information based on the at least one normalized need, the information assisting an image interpreter in interpreting the imaging procedure, wherein the first area in the reading environment is dedicated to the information and the second area in the reading environment is dedicated to showing images captured during the imaging procedure, wherein the information and the images do not overlap;
   mapping the at least one normalized need to workflow solutions, each workflow solutions associated with a set of relevant keywords, wherein the mapping occurs when the set of relevant keywords of the at least one workflow solution is included in the one normalized need and a relevance value for the set of keywords is above a predetermined threshold;
   generating an updated reading environment based on the at least one workflow solution wherein the at least one workflow solution is included in the first area of the reading environment
   generating a modified reading environment that incorporates the information into the reading environment
   transmitting the modified reading environment to an image interpreter device utilized by the image interpreter;
   receiving at least one contextual cue from the image interpreter device, wherein the at least one contextual cue comprises a specific mouse cursor gesture corresponding to a specific workflow solution; and updating the reading environment based on the at least one contextual cue.

8. The workflow server of claim 7, wherein the request is received in a free text format, and wherein the processor performs operations further comprising performing a natural language processing operation to determine at least one keyword and determining the at least one normalized need from the at least one keyword.

9. The workflow server of claim 7, wherein the request is received with at least one selection in a dedicated user interface, and wherein the processor performs operations further comprising determining the at least one normalized need from the at least one selection.

10. The workflow server of claim 7, wherein the request is received with an identification, wherein the processor performs operations further comprising determining a profile, the profile including the at least one normalized need, wherein the profile is a dedicated profile, the identification being a dedicated header that identifies the dedicated profile, and wherein the profile is a user profile, the identification being an identity of the referring physician.

11. The workflow server of claim 7, wherein the at least one workflow solutions has a serial dependency, wherein the processor performs operations further comprising determining the serial dependency and updating the reading environment based on the serial dependency.

12. A method, comprising:
at a workflow server:
receiving a request from a physician device utilized by a referring physician, the request directed to performing an imaging procedure;
determining at least one normalized need from the request filtered from a set of normalized needs associated with a predetermined data scheme listing the needs of the referring physician in a hierarchical structure based on the specialty of the referring physician, the normalized need corresponding to the referring physician;
determining at least one workflow solution based on the at least one normalized need, the at least one workflow solution respectively associated with defining a manner that the imaging procedure is to be performed;
generating a reading environment based on the at least one normalized need, the reading environment providing the at least one workflow solution, wherein a first area in the reading environment is dedicated to information based on the at least one normalized need and a second area in the reading environment is dedicated to showing images captured during the imaging procedure, wherein the information and the images do not overlap;
mapping the at least one normalized need to workflow solutions, each workflow solutions associated with a set of relevant keywords, wherein the mapping occurs when the set of relevant keywords of the at least one workflow solution is included in the one normalized need and a relevance value for the set of keywords is above a predetermined threshold;
generating an updated reading environment based on the at least one workflow solution wherein the at least one workflow solution is included in the first area of the reading environment
generating a modified reading environment that incorporates the information into the reading environment
transmitting the modified reading environment to an image interpreter device utilized by the image interpreter;
receiving at least one contextual cue from the image interpreter device, wherein the at least one contextual cue comprises a specific mouse cursor gesture corresponding to a specific workflow solution; and
updating the reading environment based on the at least one contextual cue.

* * * * *